United States Patent
Cowan et al.

[11] Patent Number: 5,967,970
[45] Date of Patent: Oct. 19, 1999

[54] SYSTEM AND METHOD FOR BALLOON-ASSISTED RETRACTION TUBE

[76] Inventors: Michael A. Cowan, 1715 Kingswood Dr., Augusta, Ga. 30904; Mark R. Lee, 807 Sparkleberry Rd., Augusta, Ga. 30809

[21] Appl. No.: 09/154,570

[22] Filed: Sep. 17, 1998

Related U.S. Application Data

[60] Provisional application No. 60/060,188, Sep. 26, 1997.

[51] Int. Cl.⁶ ..................................................... A61B 17/02
[52] U.S. Cl. .......................... 600/207; 600/206; 600/208; 600/235; 600/114
[58] Field of Search ................................... 600/201, 203, 600/204, 205, 207, 208, 206, 235, 114, 115, 116; 606/191, 192

[56] References Cited

U.S. PATENT DOCUMENTS

| | | | |
|---|---|---|---|
| 4,312,353 | 1/1982 | Shahbabian | 600/207 X |
| 4,449,532 | 5/1984 | Storz | 600/114 X |
| 4,457,300 | 7/1984 | Budde | 600/229 X |
| 5,391,178 | 2/1995 | Yapor | 606/192 |
| 5,601,590 | 2/1997 | Bonutti et al. | |
| 5,667,479 | 9/1997 | Kieturakis | 600/207 |
| 5,702,417 | 12/1997 | Hermann | 606/194 |
| 5,743,852 | 4/1998 | Johnson | 600/207 |
| 5,776,097 | 7/1998 | Massoud | 606/192 X |
| 5,782,854 | 7/1998 | Hermann | 606/194 |

OTHER PUBLICATIONS

"LEYLA Brain Retractor", Instruments for Surgery and Microsurgery (Catalog), Holco Instrument Corp., New York, NY, Item 2392–E, p. 144, 1971.

*Primary Examiner*—Jeffrey A. Smith

[57] ABSTRACT

A system and method for balloon-assisted retraction technique for the purposes of retraction of tissues and insertion of instruments in connection with advanced surgeries such as microscopic or endoscopic surgeries. A balloon assembly comprising an introducer, a balloon, and a sheath is inserted either manually or with the aid of stereotactic techniques. An endoscope may be used to ensure the proper docking of the introducer assembly. The balloon is then inflated slowly to retract the tissues, in order to create a corridor with minimal invasion. The corridor is expanded and retained using a series of dilators and retractor. The retractor comprises ports through which endoscope and other surgical instruments may pass. Surgical operation is performed through the corridor. The present invention overcomes the disadvantages of conventional retraction systems by providing better visualization and enhanced manual dexterity, as well as providing minimal invasion to allow a shorter recovery period.

30 Claims, 1 Drawing Sheet

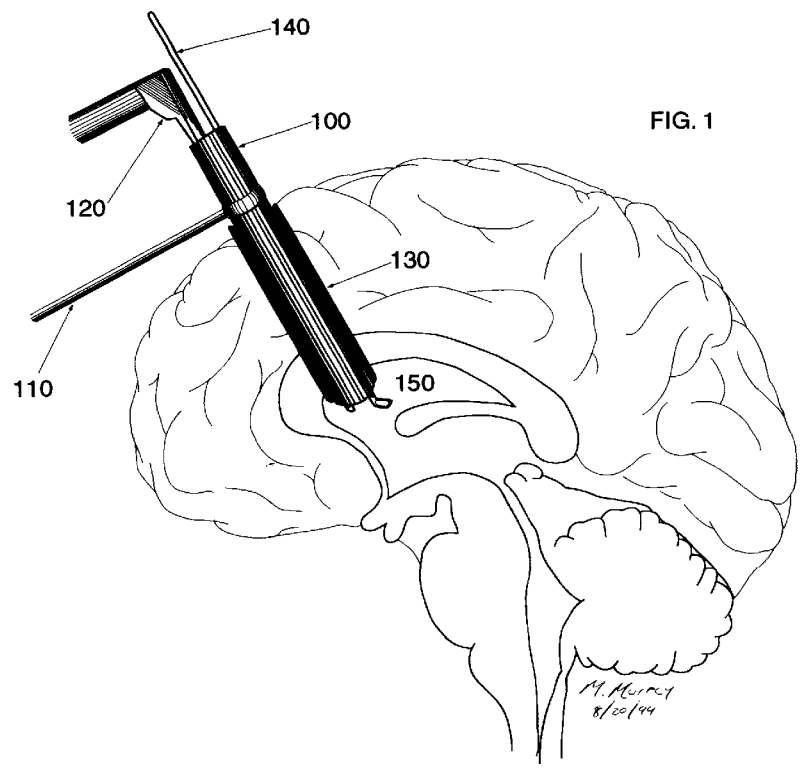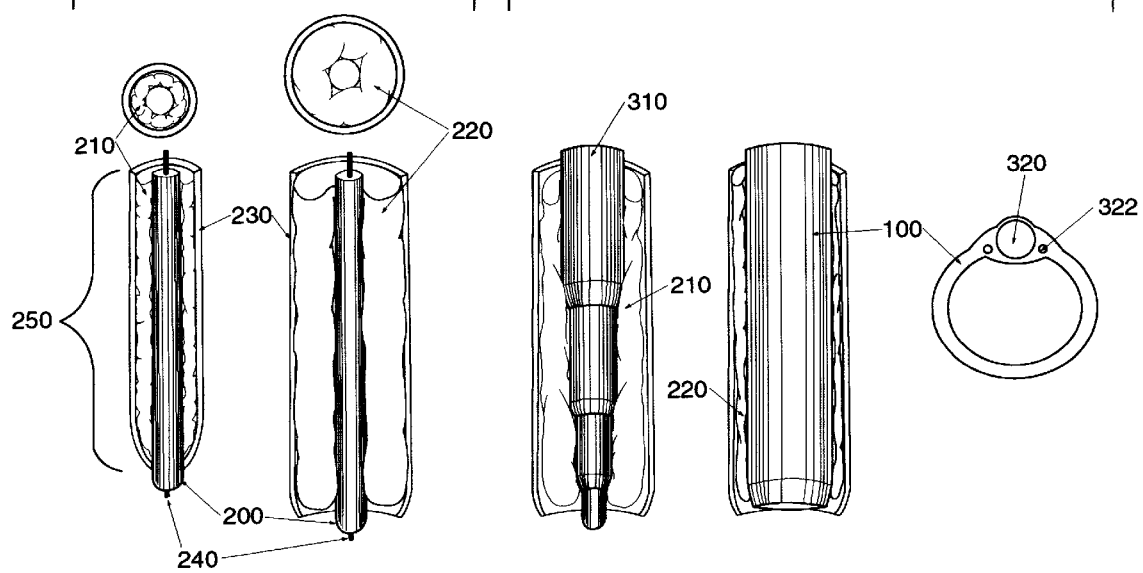

SYSTEM AND METHOD FOR BALLOON-ASSISTED RETRACTION TUBE

This application claims benefit of provisional application Ser. No. 60/060,188 filed Sep. 26, 1997.

FIELD OF THE INVENTION

The present invention generally relates to a system and method for retraction of tissues and insertion of instruments. More particularly, the present invention relates to a system and method for balloon-assisted retraction of tissues and insertion instruments in connection with surgery. Even more particularly, the present invention relates to a system and method for balloon-assisted retraction of tissues and insertion of instruments in advanced surgeries, such as microscopic or endoscopic surgery, for intracranial procedures, including supratentorial tumor resection, evacuation of spontaneous intracranial hemorrhages, ablative epilepsy surgery, treatment of intracerebral abscesses, and aneurysm clipping.

BACKGROUND OF THE INVENTION

Surgery involves a complex set of manual tasks with numerous limitations, such as a surgeon's vision and manual dexterity. Enhanced vision allows a surgeon to have a clear visual comprehension of the surgical field and manual dexterity includes a surgeon's ability to manipulate surgical instruments without unnecessary restrictions. To enhance a surgeon's vision, optimal visualization and illumination have been the driving goals behind the development of microscopic surgery and endoscopic surgery. Despite numerous advances in visualization and illumination, however, current microscopic surgery techniques still fail to be minimally invasive. Endoscopic surgery, on the other hand, in addition to being minimally invasive, provides enhanced visualization and better illumination. Current intracranial endoscopic surgery, however, still significantly limits a surgeon's ability to perform manual tasks once proper visualization and illumination are achieved.

Conventional retractor systems used in surgery include self-retaining blade retractors (e.g. Greenberg, Budde, Sugita, etc.), handheld brain ribbon, endoscopy sheaths, and microendoscopic discectomy retractor. Numerous limitations of these systems exist. For example, the self-retaining blade retractors cause excessive brain retraction, allow bleeding into field (rundown), brain swelling, as well as limited visualization and illumination. The handheld brain ribbon, in addition to having the above disadvantages, has the obvious disadvantage of requiring to be handheld, thereby reducing a surgeon's manual dexterity. Endoscopic instruments have limited utility, particularly when they are used in neurosurgical procedures. Currently available designs limit the working channel to several millimeters. This renders the surgeon to performing surgery with probe-like instruments, and thus, current neuroendoscopic intracranial neurosurgery techniques are limited to procedures with only holes or fenestrations.

Furthermore, a microendoscopic discectomy retractor can only be used for spine surgery and its dilators are not suited for other types of surgeries, such as brain surgery, because it can damage brain tissues.

Therefore, it would be desirable to have a system and method that overcomes the disadvantages of the current retractor systems, while providing enhanced illumination and visualization without sacrificing a surgeon's manual dexterity, such as the ability to manipulate surgical instruments.

SUMMARY OF THE INVENTION

The system and method of the present invention provides solutions to overcome many of the disadvantages of current microscopic and endoscopic surgery techniques.

It is an object of the present invention to provide a system and method for retraction of tissues, in order to form and retain a corridor for performing surgery.

It is another object of the present invention to provide a system and method for insertion of surgical instruments.

It is yet a further object of the present invention to provide optimal illumination and enhanced visualization.

It is another object of the present invention to facilitate manipulation of surgical instruments.

It is still a further object of the present invention to permit surgery to be performed in a minimally invasive manner, in order to make possible a shorter recovery period for the patient.

In general, in one aspect, the present invention features a system for retraction of tissues and insertion of instruments comprising a balloon, the balloon having a tubular shape, the balloon having an inner tubular surface and an outer tubular surface, the balloon having a proximal end and a distal end, the balloon having a first opening near the proximal end and through the first opening the balloon is inflated and deflated, and the balloon having a deflated state and an inflated state; and a retractor, the retractor having a tubular shape, the retractor having an inner tubular surface and an outer tubular surface, the retractor having a proximal end and a distal end, the retractor having a first opening at the proximal end and a second opening at the distal end, whereby the balloon is inserted between tissues to create a corridor, the balloon is inflated through the balloon's first opening to expand the corridor, and the retractor is inserted into the corridor to retain the corridor.

Certain implementations of the present invention may include one or more of the following features. For example, the above system further comprises an introducer, the introducer having a tubular shape, the introducer having an inner tubular surface and an outer tubular surface, the introducer having a proximal end and a distal end, the introducer having a first opening at the proximal end and a second opening at the distal end, whereby the introducer provides structural rigidity to the balloon, while the balloon is being inserted between tissues, so that the balloon may be properly placed at a desired site. Furthermore, the above system provides that the retractor having at least one port, the port being attached to the inner tubular surface of the retractor, the port having an inner circumferential surface and an outer circumferential surface, the inner circumferential surface defines a small space, whereby, after surgical instruments have been passed through the port, by limiting the freedom of their movement within the small space, the port secures the surgical instruments and the port minimizes the cross-controlling of instruments.

Among the advantages of the invention may include one or more of the following. For example, when used in brain surgery, the system and method of the present invention allows the surgery to be perform in the traditional fashion with conventional instruments, while utilizing a small corridor. Additionally, brain surgeries incorporating the present invention can be performed by practicing neurosurgeons without requiring the surgeons to undergo costly retraining.

Compared to contemporary approaches using microscope and retractors, the system and method of the present invention has numerous advantages. The present invention provides enhanced visualization, such that direct line of sight is not required, and that the surgical field is better illuminated. When used in brain surgery, the present invention allows for a smaller craniotomy, as well as less brain tissue retraction. Furthermore, the present invention can be used with stereotactic planning systems. Still further, the present invention is applicable in a number of types of surgeries, including intracranial neurosurgery and cervical spine surgery.

In contrast to current endoscopic surgical techniques, the present invention has the advantage of utilizing conventional instruments, e.g. to maximize dissection and tumor removal. The present invention also allows bleeding to be controlled using conventional means. Furthermore, the present invention allows a scope to be mounted, so that both hands of a surgeon are free to manipulate instruments.

Other features and advantages of the invention will become apparent from the following description and from the claims.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings:

FIG. 1 illustrates an embodiment of the present invention placed through the right frontal lobe into the third ventricle of the brain.

FIG. 2 illustrates an embodiment of the present invention in one state with the balloon deflated and in another state with the balloon inflated.

FIG. 3 illustrates a portion of an embodiment of the present invention comprising sequential cannulated dilators and a retractor, as well as a retractor's ports.

DETAILED DESCRIPTION OF THE PREFERRED EMBODIMENTS

A system and method for balloon-assisted retraction technique will be now be described with reference to the accompanying figures.

In the following description, for the purposes of explanation, numerous specific details are set forth in order to provide a thorough understanding of the present invention. It will be apparent, however, to one skilled in the art that the present invention may be practiced without these specific details.

FIG. 1 illustrates, in general, an exemplary system and method according to the present invention. As shown, placed through the right frontal lobe into the third ventricle of the brain, a system according to the present invention comprises a tubular retractor 100 for retracting brain tissues and for retaining a corridor 130 between the tissues created by the retraction through which surgery may be performed, a flexible arm assembly 110 for securing the retractor 100, an endoscope 120 for providing visualization, and surgical instruments 140 for suction, irrigation, etc.

In general, the system and method of the present invention comprises a balloon assembly, comprising an introducer, a balloon, and a sheath. The function of the introducer and the sheath is to provide structural rigidity to the balloon, such that the balloon may be properly placed at the desired site. The introducer may have a tubular shape having a proximal and a distal end, such that the introducer may be held at the proximal end, in order to pass the distal end through tissues to create a corridor. The sheath may be made of deformable material having stretchable, expandable properties. The sheath may be attached to the balloon in at least one location or the sheath may be a part of the balloon, such that the sheath and the balloon are constructed as one piece of material, with the sheath being the outer, more rigid surface of the balloon. The balloon may be inflated using conventional means, such as using a syringe through a pre-existing opening with solutions such as saline. The flexible arm assembly, such as those using clamps or clips or other fastening methods as attaching means, may be used to secure the retractor so that the retractor does not need to be hand-held.

FIG. 2 illustrates an embodiment of such a balloon assembly. Introducer 200 is surrounded by a deflated balloon 210, which is surrounded by a sheath 230. In the embodiment shown, with the balloon 210 in a deflated state, the entire introducer assembly 250 has a diameter of about 10 millimeters, whereas with the balloon in an inflated state 220, the introducer assembly 250 has a diameter of about 20 millimeters. A flexible endoscope 240 may be used to aid the proper docking of the introducer assembly 250 at the desired site.

In general, the system and method of the present invention may include structure, means and methods for creating and retaining a corridor surrounded by tissues, using a combination of a balloon assembly, sequential cannulated dilators, and a retractor. Alternatively, a combination of a balloon assembly and a retractor may be used. In general, a balloon is inflated slowly to create a corridor, which is then optionally enlarged by inserting sequential cannulated dilators in series. A retractor is then inserted through the corridor to retract the tissues and retain the corridor. Alternatively, sequential cannulated dilators are not used and the corridor is enlarged and retained using the retractor instead. The balloon is slowly deflated while the corridor is being enlarged. The balloon may be removed after it has served its purpose of creating a corridor.

FIG. 3 illustrates a portion of an embodiment of the present invention comprising sequential cannulated dilators 310. After the balloon 210 has been inflated, the sequential cannulated dilators 310 are inserted in series, from the smallest dilator to the largest dilator, while the balloon 220 is gradually deflated. For example, after inserting the smallest dilator over the introducer, the introducer is removed. The next larger dilator is inserted over the smallest dilator, which is then removed. The process continues until the largest dilator has been inserted. After the largest dilator has been inserted, a tubular retractor 100 with a diameter of about 20 millimeters is then inserted over the largest dilator to retain the corridor 130. The largest dilator is then removed, leaving the retractor to retain the corridor.

In general, the system and method of the present invention may include structure, means and methods for providing one or more ports to a corridor surrounded by a retractor that retains tissues, such that, through a port, surgical instruments may pass to reach a targeted tissue site at the end of the corridor. Additionally, the ports provide spatial separation between various instruments, such that the space these instruments occupy is restricted, in order to minimize cross-controlling of the instruments and to free up space in the corridor for additional instruments.

Referring to FIG. 3, a port 320, as a part of retractor 100, provides passage through the corridor 130 for endoscopic instruments, and ports 322, also a part of retractor 100, provide passage through the corridor for suction and irrigation instruments.

In general, the system and method of the present invention may include structure, as well as means and steps for inserting a balloon assembly, inflating a balloon, inserting sequential cannulated dilators followed by a tubular retractor while deflating the balloon, and optionally securing the retractor with a flexible arm assembly. Alternatively, the sequential cannulated dilators may not need to be used.

In one embodiment, the system and method of the present invention may be used in intracranial neurosurgery involving endoscopic and stereotactic techniques. For the purposes of illustration, the present invention is placed through the right frontal lobe into the third ventricle of the brain. An embodiment of the present invention comprises the following. First, referring to FIGS. 1 and 2, a 10 millimeter balloon assembly 250 comprising an introducer 200, a deflated balloon 210, and sheath 230, is placed either manually or using the aid of stereotactic techniques into the third ventricle 150 of the brain. If desired, a small flexible endoscope 240 may be passed through the introducer 200 to provide visualization for proper docking. Second, the deflated balloon 210 contained within the sheath 230 and surrounding the introducer 200 is inflated slowly over the course of ten to fifteen minutes, while simultaneously administering intravenous mannitol and performing spinal drainage, in order to relax the brain tissues as much as possible. The slow inflating of the balloon allows the brain tissues to accommodate the corridor created by the inflating balloon with minimal disturbance. Third, sequential cannulated dilators 310 are inserted between the introducer 200 and the inflated balloon 210 in series, from the smallest dilator to the largest dilator, while simultaneously deflating the balloon 220. The introducer is removed after the smallest dilator has been inserted over the introducer to expand and to retain the corridor initially created by the introducer and the inflated balloon. The smallest dilator is removed after a next larger dilator has been inserted over it to continue to expand and retain the corridor. This process continues until the largest dilator has been inserted. Fourth, a tubular retractor 100 of about 20 millimeter in diameter is inserted between the largest dilator 310 and the deflated balloon 220, which is then removed. Finally, the retractor 100 is secured in place with a flexible arm assembly 110. Alternatively, the sequential cannulated dilators 310 may not need to be used, and the retractor 100 may be inserted directly over the introducer 200 and within the balloon to retain the corridor.

Surgery can then be performed through the established corridor. An endoscope 120 may be mounted on the wall of the retractor 100 through a port 320 to provide visualization. Instruments such additional flexible scopes, or such as those for irrigation or suction may be passed through other ports 322 on the retractor 100. Furthermore, the ports 320 and 322 may be modified with ratcheting devices so that the instruments may be secured at appropriate levels in the operative field.

In the foregoing specification, the invention has been described in reference to specific embodiments thereof Other embodiments are within the scope of the following claims. For example, a balloon assembly may comprise of parts other than an introducer, a balloon and a sheath. Furthermore, a balloon assembly with the balloon in a deflated state may be of a size other than 10 millimeters, and a balloon assembly with the balloon in an inflated state may be of a size other than 20 millimeters.

What is claimed is:

1. A system for retraction of tissues and insertion of instruments comprising:
   a balloon, the balloon having a tubular shape, the balloon having an inner tubular surface and an outer tubular surface, the balloon having a proximal end and a distal end, the balloon having a first opening near the proximal end and through the first opening the balloon is inflated and deflated, and the balloon having a deflated state and an inflated state;
   a retractor, the retractor having a tubular shape, the retractor having an inner tubular surface and an outer tubular surface, the retractor having a proximal end and a distal end, the retractor having a first opening at the proximal end and a second opening at the distal end; and
   sequential cannulated dilators, the dilators having a tubular shape, the dilators having an inner tubular surface and an outer tubular surface, the dilators having a proximal end and a distal end, the dilators having a first opening at the proximal end and a second opening at the distal end, the dilators having increasing circumferences,
   whereby
      the balloon is inserted between tissues to create a corridor, the balloon is inflated through the balloon's first opening to expand the corridor;
      the retractor is inserted into the corridor to retain the corridor; and
      the dilators are inserted in series, from the dilator having the smallest circumference to the dilator having the largest circumference, such that the dilator having the smallest circumference is inserted first, then a dilator having the next larger circumference is inserted over the dilator having the smallest circumference, such that this process is repeated until the retractor is inserted over the dilator having the largest circumference, in order to expand and retain the corridor.

2. A system according to claim 1 further comprising:
   an introducer, the introducer having a tubular shape, the introducer having an inner tubular surface and an outer tubular surface, the introducer having a proximal end and a distal end, the introducer having a first opening at the proximal end and a second opening at the distal end,
   whereby the introducer provides structural rigidity to the balloon, while the balloon is being inserted between tissues, so that the balloon may be properly placed at a desired site.

3. A system according to claim 2 further comprising:
   a flexible endoscope, wherein the flexible endoscope is passed through the introducer via the introducer's first opening and second opening,
   whereby the flexible endoscope ensures that the balloon is inserted at a desired site.

4. A system according to claim 1 further comprising:
   a sheath, the sheath having a tubular shape, the sheath having an inner tubular surface and an outer tubular surface, the sheath having a proximal end and a distal end, the sheath being made of deformable material, the material having properties for expanding and stretching, the sheath being attached to the balloon in at least one location,
   whereby the sheath provides structural rigidity to the balloon, while the balloon is being inserted between tissues, so that the balloon may be properly placed at a desired site.

5. A system according to claim 1 further comprising:
   a sheath, the sheath being a part of the balloon, the sheath forming at least a part of the outer tubular surface of the balloon, the sheath being made of deformable material, the material having properties for expanding and stretching, whereby the sheath provides structural rigidity to the balloon, while the balloon is being inserted between tissues, so that the balloon may be properly placed at the desired site.

6. A system according to claim 1 further comprising:

a flexible arm assembly, the flexible arm assembly having attaching means, whereby the flexible arm assembly secures the retractor in a fixed position so that the retractor need not be hand-held.

7. A system according to claim 1, wherein the balloon's outer circumference is about 10 millimeters when the balloon is in a deflated state, and the balloon's outer circumference is about 20 millimeters when the balloon is in an inflated state.

8. A system for retraction of tissues and insertion of instruments comprising:

a balloon, the balloon having a tubular shape, the balloon having an inner tubular surface and an outer tubular surface, the balloon having a proximal end and a distal end, the balloon having a first opening near the proximal end and through the first opening the balloon is inflated and deflated, and the balloon having a deflated state and an inflated state; and a retractor, the retractor having a tubular shape, the retractor having an inner tubular surface and an outer tubular surface, the retractor having a proximal end and a distal end, the retractor having a first opening at the proximal end and a second opening at the distal end, wherein the retractor having at least one port, the port being attached to the inner tubular surface of the retractor, the port having an inner circumferential surface and an outer circumferential surface, the inner circumferential surface defines a small space, whereby the balloon is inserted between tissues to create a corridor, the balloon is inflated through the balloon's first opening to expand the corridor;

the retractor is inserted into the corridor to retain the corridor; and after surgical instruments have been passed through the port, by limiting the freedom of their movement within the small space, the port secures the surgical instruments and the port minimizes the cross-controlling of instruments.

9. A system according to claim 8 further comprising:

an introducer, the introducer having a tubular shape, the introducer having an inner tubular surface and an outer tubular surface, the introducer having a proximal end and a distal end, the introducer having a first opening at the proximal end and a second opening at the distal end, whereby the introducer provides structural rigidity to the balloon, while the balloon is being inserted between tissues, so that the balloon may be properly placed at a desired site.

10. A system according to claim 9 further comprising:

a flexible endoscope, wherein the flexible endoscope is passed through the introducer via the introducer's first opening and second opening, whereby the flexible endoscope ensures that the balloon is inserted at a desired site.

11. A system according to claim 8 further comprising:

a sheath, the sheath having a tubular shape, the sheath having an inner tubular surface and an outer tubular surface, the sheath having a proximal end and a distal end, the sheath being made of deformable material, the material having properties for expanding and stretching, the sheath being attached to the balloon in at least one location, whereby the sheath provides structural rigidity to the balloon, while the balloon is being inserted between tissues, so that the balloon may be properly placed at a desired site.

12. A system according to claim 8 further comprising:

a sheath, the sheath being a part of the balloon, the sheath forming at least a part of the outer tubular surface of the balloon, the sheath being made of deformable material, the material having properties for expanding and stretching, whereby the sheath provides structural rigidity to the balloon, while the balloon is being inserted between tissues, so that the balloon may be properly placed at the desired site.

13. A system according to claim 8 further comprising:

a flexible arm assembly, the flexible arm assembly having attaching means, whereby the flexible arm assembly secures the retractor in a fixed position so that the retractor need not be hand-held.

14. A system according to claim 8, wherein the balloon's outer circumference is about 10 millimeters when the balloon is in a deflated state, and the balloon's outer circumference is about 20 millimeters when the balloon is in an inflated state.

15. A system according to claim 8, wherein the surgical instruments comprising an endoscope and instruments for irrigation or suction or both.

16. A method for retraction of tissues and insertion of instruments comprising:

inserting a balloon through tissues, the balloon having a tubular shape, the balloon having an inner tubular surface and an outer tubular surface, the balloon having a proximal end and a distal end, the balloon having a first opening at the proximal end and through the first opening the balloon is inflated and deflated, and the balloon having a deflated state and an inflated state;

inserting a retractor, the retractor having a tubular shape, the retractor having an inner tubular surface and an outer tubular surface, the retractor having a proximal end and a distal end, the retractor having a first opening at the proximal end and a second opening at the distal end; and inserting sequential cannulated dilators in series, the dilators having a tubular shape, the dilators having an inner tubular surface and an outer tubular surface, the dilators having a proximal end and a distal end, the dilators have increasing circumferences, from the dilator having the smallest circumference to the dilator having the largest circumference, the inserting is performed such that the dilator having the smallest circumference is inserted first, then a dilator having the next larger circumference is inserted over the dilator having the smallest circumference, such that this process is repeated until the retractor is inserted over the dilator having the largest circumference, in order to expand and retain the corridor, whereby the balloon is inserted between the tissues to create a corridor, the balloon is inflated to expand the corridor, and the retractor is inserted into the corridor to retain the corridor.

17. A method according to claim 16, further comprising:

inserting an introducer through tissues, the introducer having a tubular shape, the introducer having an inner tubular surface and an outer tubular surface, the introducer having a proximal end and a distal end, the introducer having an opening at the proximal end and a second opening at the distal end, whereby the introducer provides structural rigidity to the balloon, while the balloon is being inserted between tissues, so that the balloon may be properly placed at a desired site.

18. A method according to claim 17, further comprising:

inserting a flexible endoscope, whereby the flexible endoscope is passed through the introducer's first opening and second opening to ensure that the balloon is inserted at a desired site.

19. A method according to claim 16, wherein inserting the balloon also inserts a sheath, the sheath having a tubular shape, the sheath having an inner tubular surface and an outer tubular surface, the sheath having a proximal end and a distal end, the sheath is made of deformable material, the material having properties for expanding and stretching, the sheath being attached to the balloon in at least one location, whereby the sheath provides structural rigidity to the balloon, while the balloon is being inserted between tissues, so that the balloon may be properly placed at a desired site.

20. A method according to claim 16, wherein inserting the balloon also inserts a sheath, the sheath being a part of the balloon, the sheath forming at least a part of the outer tubular surface of the balloon, the sheath being made of deformable material, the material having properties for expanding and stretching, whereby the sheath provides structural rigidity to the balloon, while the balloon is being inserted between tissues, so that the balloon may be properly placed at the desired site.

21. A method according to claim 16, further comprising:

securing a flexible arm assembly to the retractor, the flexible arm assembly having attaching means, whereby the flexible arm assembly secures the retractor in a fixed position so that the retractor need not be hand-held.

22. A method according to claim 16, further comprising:

inflating the balloon which changes the balloon from a deflated state to an inflated state, whereby the outer circumference of the balloon is about 10 millimeters when the balloon is in a deflated state, and the outer circumference of the balloon is about 20 millimeters when the balloon is in an inflated state.

23. A method for retraction of tissues and insertion of instruments comprising:

inserting a balloon through tissues, the balloon having a tubular shape, the balloon having an inner tubular surface and an outer tubular surface, the balloon having a proximal end and a distal end, the balloon having a first opening at the proximal end and through the first opening the balloon is inflated and deflated, and the balloon having a deflated state and an inflated state;

inserting a retractor, the retractor having a tubular shape, the retractor having an inner tubular surface and an outer tubular surface, the retractor having a proximal end and a distal end, the retractor having a first opening at the proximal end and a second opening at the distal end; and inserting instruments through at least one port, the port being attached to the inner tubular surface of the retractor, the port having an inner circumferential surface and an outer circumferential surface, the inner circumferential surface defines a small space, whereby the balloon is inserted between the tissues to create a corridor, the balloon is inflated to expand the corridor;

the retractor is inserted into the corridor to retain the corridor; and after surgical instruments have been passed through the port, by limiting the freedom of their movement within the small space, the port secures the surgical instruments and the port minimizes the cross-controlling of instruments.

24. A method according to claim 23, further comprising:

inserting an introducer through tissues, the introducer having a tubular shape, the introducer having an inner tubular surface and an outer tubular surface, the introducer having a proximal end and a distal end, the introducer having an opening at the proximal end and a second opening at the distal end, whereby the introducer provides structural rigidity to the balloon, while the balloon is being inserted between tissues, so that the balloon may be properly placed at a desired site.

25. A method according to claim 24, further comprising:

inserting a flexible endoscope, whereby the flexible endoscope,is passed through the introducer's first opening and second opening to ensure that the balloon is inserted at a desired site.

26. A method according to claim 23, wherein inserting the balloon also inserts a sheath, the sheath having a tubular shape, the sheath having an inner tubular surface and an outer tubular surface, the sheath having a proximal end and a distal end, the sheath is made of deformable material, the material having properties for expanding and stretching, the sheath being attached to the balloon in at least one location, whereby the sheath provides structural rigidity to the balloon, while the balloon is being inserted between tissues, so that the balloon may be properly placed at a desired site.

27. A method according to claim 23, wherein inserting the balloon also inserts a sheath, the sheath being a part of the balloon, the sheath forming at least a part of the outer tubular surface of the balloon, the sheath being made of deformable material, the material having properties for expanding and stretching, whereby the sheath provides structural rigidity to the balloon, while the balloon is being inserted between tissues, so that the balloon may be properly placed at the desired site.

28. A method according to claim 23, further comprising:

securing a flexible arm assembly to the retractor, the flexible arm assembly having attaching means, whereby the flexible arm assembly secures the retractor in a fixed position so that the retractor need not be hand-held.

29. A method according to claim 23, further comprising:

inflating the balloon which changes the balloon from a deflated state to an inflated state, whereby the outer circumference of the balloon is about 10 millimeters when the balloon is in a deflated state, and the outer circumference of the balloon is about 20 millimeters when the balloon is in an inflated state.

30. A method according to claim 23, wherein the inserting of surgical instruments comprising inserting an endoscope and instruments for irrigation or suction or both.

* * * * *